United States Patent [19]

Binder

[11] 4,352,819
[45] Oct. 5, 1982

[54] NOVEL 1-[3-(2-HYDROXY-3-ALKYLAMINO-PROPOXY)-2-THIENYL]-3-PHENYL-1-PROPANONES AND THEIR SALTS AND A PROCESS FOR THE PREPARATION THEREOF

[75] Inventor: Dieter Binder, Vienna, Austria

[73] Assignee: Laevosan-Gesellschaft mbH & Co. KG, Linz, Austria

[21] Appl. No.: 324,760

[22] Filed: Nov. 25, 1981

[30] Foreign Application Priority Data

Nov. 28, 1980 [AT] Austria .................................. 5818/80

[51] Int. Cl.³ ..................... A61K 31/38; C07D 333/16
[52] U.S. Cl. ........................................ 424/275; 549/64
[58] Field of Search ............................ 424/275; 549/64

[56] References Cited

U.S. PATENT DOCUMENTS 4,123,550 10/1978 Untch et al. ........................... 549/64

*Primary Examiner*—Alan Siegel
*Attorney, Agent, or Firm*—Sughrue, Mion, Zinn, Macpeak & Seas

[57] ABSTRACT

The disclosure is directed to novel 1-[3-(2-hydroxy-3-alkylaminopropoxy)-2-thienyl]-3-phenyl-1-propanones and their salts. The compounds of the invention have the structural formula

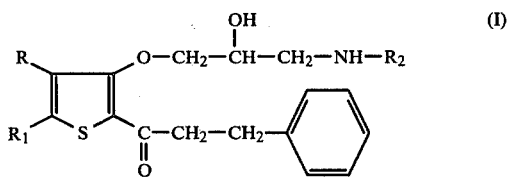

in which R and $R_1$ are independently hydrogen or methyl and $R_2$ is n-propyl, n-butyl, isobutyl or tert-butyl. The compounds have an outstanding antiarrhytmical activity already in low doses.

8 Claims, No Drawings

NOVEL 1-[3-(2-HYDROXY-3-ALKYLAMINOPROPOXY)-2-THIENYL]-3-PHENYL-1-PROPANONES AND THEIR SALTS AND A PROCESS FOR THE PREPARATION THEREOF

SUMMARY OF INVENTION

The present invention relates to novel derivatives of the 1-[3-(2-hydroxy-3-alkylaminopropoxy)-2-thienyl]-3-phenyl-1-propanone of the general formula

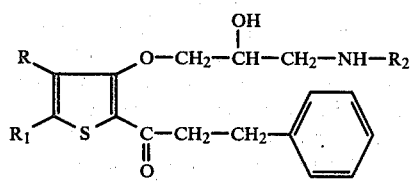

in which R and $R_1$ are independently hydrogen or methyl and $R_2$ is n-propyl, n-butyl, isobutyl or tert-butyl, and the acid addition salts thereof, which compounds have a therapeutically valuable activity, and a process for the preparation thereof.

The process of the invention comprises the reaction of a compound of general formula

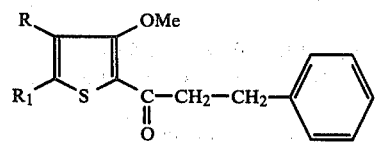

in which R and $R_1$ are as defined above and Me is the cation of an alkali metal, with epichlorohydrin of the formula

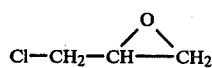

and reaction of the compound of formula

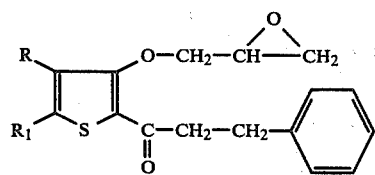

thus obtained, in which R and $R_1$ are as defined above, with an alkylamine of the general formula

in which $R_2$ is as defined above, and, if desired, conversion of an obtained base of formula (I) into an acid addition salt.

The novel compounds of general formula (I) have already in low doses an outstanding antiarrhythmic activity on the awake dog. They are active when they are administered orally.

A preferred class is that of compounds of formula (I) in which $R_2$ is n-propyl.

DETAILED DESCRIPTION OF THE INVENTION

Due to their pharmacological properties the novel compounds and their acid addition salts may be used alone or in admixture with other active substances in form of a usual galenic preparation (also retarding forms) for the treatment of disorders of the heart rhythm.

The reaction of the compound (II) with the compound (III) according to the invention is carried out preferably in an inert solvent, especially preferably in an excess of epichlorhydrine at temperatures between 110° und 140° C.

The reaction of the intermediate compound (IV) with the compound (V) is carried out preferably in an inert solvent, especially preferably in an excess of the amine (V) at a temperature between 50° and 100° C.

The acid addition salts of the compounds of formula (I) can be converted in a manner known per se into the free bases, e.g. with alkalis or ion exchangers. By reaction with inorganic or organic acids, especially those which are suitable for the formation of therapeutically useful salts, other salts can be recovered from the above mentioned bases.

Due to the close relation between the novel compounds and the salts thereof the expression "free bases" comprises analogously and conveniently also the corresponding salts.

The starting materials of the formulae (III) and (V) are known from the literature.

Compounds of formula (II) can be prepared from the free compounds (Me=H) most conveniently by means of alkaline hydroxides, alkaline hydrides or alkaline alcoholates.

The free compounds of formula (II) can be prepared according to the following reaction scheme starting from the known compounds of formula (VI):

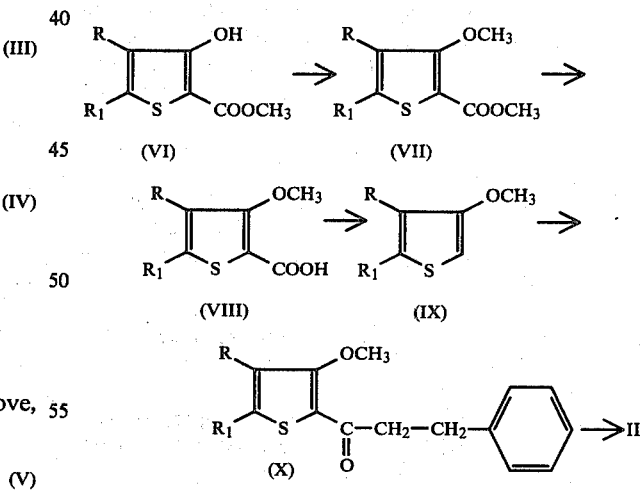

The following example illustrates the invention without limiting it thereto.

EXAMPLE

1-[3-(2,3-Epoxypropoxy)-2-thienyl]-3-phenyl-1-propanone (formula IV: R and $R_1$=H)

1.74 g (0.076 moles) of sodium were dissolved in 50 ml of absolute methanol, 17.55 g (0.076 moles) of 1-(3- hydroxy-2-thienyl)-3-phenyl-1-propanone (formula II: R and $R_1$=H, Me=H) were added and the solution was evaporated (in vacuo) to dryness. 50 ml of epichlorohydrin (III) were added to the crystalline residue (formula II: R and $R_1$=H, Me=Na) and refluxed for 4 hours. The reaction mixture was filtered over Hyflo, rinsed with some benzene und the filtrate was evaporated in vacuo. The crystalline residue was heated up in 1250 ml of cyclohexane with addition of carbon, filtered over Hyflo and the filtrate was evaporated in vacuo. The weight of the crystalline residue was 16.9 g (77.6%). The product was sufficiently pure for the further use. Melting point (cyclohexane) 59°-61° C.

The following compounds can be obtained analogously:

1-[3-(2,3-epoxypropoxy)-4-methyl-2-thienyl]-3-phenyl-1-propanone (formula IV: R=$CH_3$, $R_1$=H), oil, not isolated;

1-[3-(2,3-epoxypropoxy)-5-methyl-2-thienyl]-3-phenyl-1-propanone (formula IV: R=H, $R_1$=$CH_3$), oil, not isolated;

1-[4,5-dimethyl-3-(2,3-epoxypropoxy)-2-thienyl]-3-phenyl-1-propanone (formula IV; R and $R_1$=$CH_3$), oil, not isolated, $n_D^{20}$=1.5535.

1-[3-(2-Hydroxy-3-n-propylaminopropoxy)-2-thienyl]-3-phenyl-1-propanone-chlorohydrate (formula I.HCl: R and $R_1$=H, $R_2$=n-propyl)

14.4 g (0.05 moles) of crude 1-[3-(2,3-epoxypropoxy)-2-thienyl]-3-phenyl-1-propanone (formula IV: R and $R_1$=H) were refluxed in 40 ml of n-propylamine (formula V: $R_2$=propyl) for 4 hours with stirring. The reaction mixture was evaporated in vacuo, the residue was distributed between 250 ml of $CH_2Cl_2$ and 150 ml of 1 N hydrochloric acid, the phases were separated, the aqueous phase was extracted with 2×50 ml of $CH_2Cl_2$ and the combined organic phases were dried ($Na_2SO_4$) and evaporated in vacuo. The crude product obtained in crystalline form could be recrystallized from acetone/methanol 8:2 (about 120 ml) with carbon. Yield 12.2 g (64%) of colorless crystals, melting point 150°-152° C.

The following compounds can be obtained in analogous manner:

1-[3-(2-hydroxy-3-n-butylaminopropoxy)-2-thienyl]-3-phenyl-1-propanone-chlorohydrate (formula I: R and $R_1$=H, $R_2$=n-butyl), melting point (from acetone): 113°-114° C.;

1-[3-(2-hydroxy-3-n-tert-butylaminopropoxy)-2-thienyl]-3-phenyl-1-propanone-chlorohydrate (formula I: R and $R_1$=H, $R_2$=tert-butyl), melting point (from acetone): 143°-144° C.

1-[4-methyl-3-(2-hydroxy-3-n-propylaminopropoxy)-2-thienyl]-3-phenyl-1-propanone-chlorohydrate (formula I: R=$CH_3$, $R_1$=H, $R_2$=n-propyl), melting point: 107°-111° C. (methanol/ether);

1-[5-methyl-3-(2-hydroxy-3-n-propylamino-propoxy)-2-thienyl]-3-phenyl-1-propanone-chlorohydrate (formula I: R=H, $R_1$=$CH_3$, $R_2$=n-propyl), melting point: 203°-205° C. (from methanol);

1-[4,5-dimethyl-3-(2-hydroxy-3-n-propylaminopropoxy)-2-thienyl]-3-phenyl-1-propanone-chlorohydrate (formula I: R and $R_1$=$CH_3$, $R_2$=n-propyl), melting point: 126°-128° C. (toluene/ether).

The starting compound can be obtained as follows:

3-Methoxy-thiophene-2-carboxylic acid (formula VIII: R and $R_1$=H)

13.5 g (0.085 moles) of 3-hydroxythiophene-2-carboxylic acid methyl ester (VI: R and $R_1$=H) were added to a solution of 36 g (0.34 moles) of $Na_2CO_3$ in 145 ml of $H_2O$ and boiled up for a short time with stirring. Then within of 15 minutes 21.53 g (0.17 moles) of dimethylsulfate are dropped thereto, the temperature of the reaction mixture being maintained just below the boiling point. After completion of the addition the heating was continued for 20 minutes on reflux, the reaction mixture was cooled and extracted several times with $CH_2Cl_2$. The combined organic phases were extracted three-times with 2 N NaOH, dried ($Na_2SO_4$) and evaporated. The oily residue consisting of 3-methoxy-thiophene-2-carboxylic acid methyl ester (VII: R and $R_1$=H) has a weight of 7.1 g. This residue was dissolved in a solution of 2.54 g (0.045 moles) of KOH in 70 ml of methanol and refluxed for 30 minutes. Then the methanol was distilled off in vacuo and the residue was distributed between water and $CH_2Cl_2$. The aqueous phase was acidified with concentrated HCl and the precipitated colorless crystals were filtered off. Yield: 5.7 g (54%), melting point 180°-183° C.

The following compounds can be obtained in analogous manner:

3-methoxy-4-methyl-thiophene-2-carboxylic acid (formula VIII: R=$CH_3$, $R_1$=H), melting point: 119°-121° C.;

3-methoxy-5-methyl-thiophene-2-carboxylic acid (formula VIII: R=H, $R_1$=$CH_3$), melting point: 175°-177° C.;

4,5-dimethyl-3-methoxy-thiophene-2-carboxylic acid (formula VIII: R+$R_1$=$CH_3$), melting point: 133°-135° C.

3-Methoxythiophene (IX: R and $R_1$=H)

57 g of 3-methoxythiophene-2-carboxylic acid (formula VIII: R and $R_1$=H) were triturated with 15 g of Cu-powder and transferred into a distilling flask connected with a distilling condenser having a collecting means. In the apparatus a vacuum of 65 mm Hg is applied and the distilling flask is heated to 150°-180° C. The 3-methoxythiophene distilling off is collected in the collecting means. Yield: 33 g (80%).

The following compounds are obtained in analogous manner:

3-Methoxy-4-methyl-thiophene (formula IX: R=$CH_3$, $R_1$=H), boiling point: 83° C./30 mm Hg;

3-methoxy-5-methyl-thiophene (formula IX: R=H, $R_1$=$CH_3$), boiling point: 63°-65° C./16 mbar;

4,5-dimethoxy-3-methoxy-thiophene (formula IX: R and $R_1$=$CH_3$), boiling point: 78°-84° C./10 mm Hg.

1-(3-Hydroxy-2-thienyl)-3-phenyl-2-propanone (formula II: R and $R_1$=H)

44.9 g (0.266 moles) of 3-phenylpropionic acid chloride were dissolved in 400 ml of absolute $CHCl_3$. Then 69.37 g (0.266 moles) of $SnCl_4$ in 50 ml of $CHCl_3$ were dropped thereto. Then the temperature of the mixture was increased to 15° C. and 30.4 g (0.266 moles) of 3-methoxythiophene (formula IX: R and $R_1$=H) dissolved in 250 ml of $CHCl_3$ were dropped thereto within 30 minutes. The stirring was continued for 20 minutes.

The reaction mixture was poured on semi-concentrated HCl and the organic phase was separated and extracted twice with $CH_2Cl_2$. The combined organic phases were extracted three-times with a solution of $NaHCO_3$, dried ($Na_2SO_4$) and evaporated. The oily residue (57%) consisting mainly of 1-(3-methoxy-2-thienyl)-3-phenyl-1-propanone (formula X: R and $R_1 = H$) was dissolved in 270 ml of nitrobenzene and added to a solution of 62 g of anhydrous $AlCl_3$ in 270 ml of nitrobenzene. The reaction mixture was stirred at 70°–90° C. for 1.5 hours, cooled, poured onto ice/HCl and allowed to stand over night at room temperature. Then the phases were separated, the aqueous phase extracted twice with $CH_2Cl_2$, the combined organic phases were extracted three-times with 2 N NaOH, the combined NaOH-phases were acidified with concentrated HCl and the precipitating product was extracted three-times with $CH_2Cl_2$. After evaporation of the combined $CH_2Cl_2$-phases the dark crystalline residue was dissolved in benzene, filtered over silica gel and washed thoroughly. After evaporation of the filtrate 29.1 g (47%) of pure product were obtained, melting point (methanol): 50° C.

The following compounds are obtained in analogous manner:

1-(3-hydroxy-4-methyl-2-thienyl)-3-phenyl-1-propanone (formula II, $R = CH_3$, $R_1 = H$), melting point: 36°–38° C. (methanol);

1-(3-hydroxy-5-methyl-2-thienyl)-3-phenyl-1-propanone (formula II: $R = H$, $R_1 = CH_3$), oil, $n_D^{20} = 1.6014$;

1-(4,5-dimethyl-3-hydroxy-2-thienyl)-3-phenyl-1-propanone (formula II: R and $R_1 = CH_3$), melting point (toluene/ether): 43°–46° C.

When studying the antiarrhytmic potency of a substance, protection is measured by the decrease in the incidence of ventricular ectopic beats or ventricular fibrillation following the administration of the compound under test. Depending on the protocol, either the animals are their own controls, or the animals are separated into two groups, namely control group and treated group.

These compounds were first selected owing to their activity in different experimental arrhythmia models which are used as screening techniques. So the chloroform, aconitine and calcium chloride tests have been used for testing the compounds of the invention as described by J. W. Lawson, J.Pharmacol.exp.Ther. 160, 22–81 (1968) "Antiarrhythmic activity of some isoquinoline derivatives determined by a rapid screening procedure in the mouse".

Code numbers:

LG 80-6-00 = 1-[3-(2-hydroxy-3-n-butylaminopropoxy)-2-thienyl]-3-phenyl-1-propanone-chlorohydrate LG 80-6-01 = 1-[4-methyl-3-(2-hydroxy-3-n-propylaminopropoxy)-2-thienyl]-3-phenyl-1-propanone-chlorohydrate LG 80-6-02 = 1-[5-methyl-3-(2-hydroxy-3-n-propylaminopropoxy)-2-thienyl]-3-phenyl-1-propanone-chlorohydrate Prop. = Propafenone.

CHLOROFORM TEST

Five minutes after i.v. injection of the compound under study the mice are placed into a 300 ml beaker containing cotton wool soaked with 20 ml of chloroform. The animals are watched carefully and taken out of the beaker as soon as the second respiratory arrest occured. The heart is then quickly exposed to visual inspection of ventricular rhythm (see Lawson, Loc.-cit.). The $ED_{50}$ is the dose of the compound which protects 50% of the mice against ventricular fibrillation induced by chloroform. The following Table shows the $ED_{50}$ of the new compounds LG 80-6-00, LG 81-6-01, LG 81-6-02 and of the reference compound Propafenon.

ACONITINE TEST

It seems that investigators favour the rat so as to study the protective effect of a compound on arrhythmia induced by aconitine (see: J. L. Junien et al., Arzneim.Forsch. 24, 1743–1747 (1974); L. Szekeres et al., Experimental cardiac arrhythmias and antiarrhythmic drugs, Publishing House of the Hungarian Academy of Sciences (Akadèmia Kiado), Budapest (1971); M. R. Malinow et al., Arch.int.Pharmacodyn. 102, 55–64 (1955); C. Bianchi et al., Arzneim. Forsch. 18, 845–850 (1968); B. B. Vargaftig et al., J. Pharm. Pharmacol. 27, 697–699 (1975); and M. Fekete et al., Med Exp. 10, 93–102 (1964)).

Test compounds are administered to the urethane-anaesthetized rat prior to the injection of aconitine. Various antiarrhythmic drugs are capable of delaying the onset of aconitine-induced arrhythmias and this model of arrhythmia seems to be suitable for assaying the antiarrhythmic acitivity.

The following table shows the results of the test with respect to the $ED_{50}$ of LG 80-6-00, LG 81-6-01, LG 81-6-02 and Propafenon. It is evident that the best compound in this method is the LG 81-6-01.

CALCIUM CHLORIDE TEST

Cardiac arrhythmia frequently occurs when the levels of serum ions are abnormal, particularly when the calcium level is four times higher than the normal concentration. This is the reason why intravenous administraction of high doses of calcium chloride can elicit the development of dysrhythmias in animals.

In the anaesthetized rat the rapid intravenous injection of calcium chloride causes lethal ventricular fibrillation or ventricular extrasystoles. The evaluation of the activity of the test compound aministered prior to the calcium chloride injection is based on the onset of arrhythmia (M. R. Malinow et al., Arch.int. Pharmacodyn. 102, 55–64 (1955), "The pharmacology of experimental ventricular arrhythmias in the rat I. Antihistamic drugs") or return to sinus rhythm after occasional trouble of rhythm (M. Fekete et al., Med. Exp. 10, 93–102 (1964), "On the antiarrhythmic effect of some thymoleptics: amitriptyline, imipramine, trimepropimine and desmethylimipramine").

The compounds of the invention have shown to possess protective effects against calcium chloride-induced arrhythmias. The $ED_{50}$ of the compounds of the invention compared with the control compound Propafenon are listed in the following Table. It is evident that LG 81-6-01 gives the best protection against arrhythmias induced by calcium chloride.

TABLE

| Test compound | $ED_{50}$ mg/kg bodyweight | | |
|---|---|---|---|
| | Chloroform mouse | Aconitine rat | Calcium chloride rat |
| LG 80-6-00 | 4,16 | 4,23 | 5,04 |
| LG 80-6-01 | 3,57 | 1,49 | 2,59 |
| LG 80-6-02 | 17,57 | 22,8 | 2,87 |

| | ED$_{50}$ mg/kg bodyweight | | |
|---|---|---|---|
| Test compound | Chloroform mouse | Aconitine rat | Calcium chloride rat |
| Propafenon | 3,45 | 2,10 | 4,49 |

What is claimed is:

1. A 1-[3-(2-hydroxy-3-alkylaminopropoxy)-2-thienyl]-3-phenyl-1-propanone of the formula

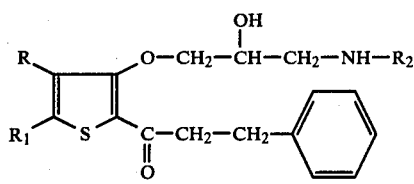

in which R and R$_1$ are independently hydrogen or methyl and R$_2$ is n-propyl, n-butyl, isobutyl or tert-butyl and an acid addition salt thereof.

2. 1-[3-(2-Hydroxy-3-n-propylaminopropoxy)-2-thienyl]-3-phenyl-1-propanone-chlorohydrate according to claim 1.

3. 1-[3-(2-Hydroxy-3n-butylaminopropoxy)-2-thienyl]-3-phenyl-1-propanone-chlorohydrate according to claim 1.

4. 1-[3-(2-Hydroxy-3-n-tert-butylaminopropoxy)-2-thienyl]-3-phenyl-1-propanone-chlorohydrate according to claim 1.

5. 1-[4-Methyl-3-(2-hydroxy-3-n-propylaminopropoxy)-2-thienyl]-3-phenyl-1-propanone-chlorohydrate according to claim 1.

6. 1-[5-Methyl-3-(2-hydroxy-3-n-propylaminopropoxy)-2-thienyl]-3-phenyl-1-propanone-chlorohydrate according to claim 1.

7. 1-[4,5-Dimethyl-3-(2-hydroxy-3-n-propylaminopropoxy)-2-thienyl]-3-phenyl-1-propanone-chlorohydrate according to claim 1.

8. A pharmaceutically active composition comprising an effective amount of a compound of claim 1, 2, 3, 4, 5, 6 or 7 together with a pharmaceutically acceptable carrier or diluent.